United States Patent
Swartz et al.

(12)

(10) Patent No.: US 6,337,191 B1
(45) Date of Patent: Jan. 8, 2002

(54) VITRO PROTEIN SYNTHESIS USING GLYCOLYTIC INTERMEDIATES AS AN ENERGY SOURCE

(75) Inventors: James Swartz, Menlo Park; Dong-Myung Kim, Palo Alto, both of CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 09/621,339

(22) Filed: Jul. 21, 2000

Related U.S. Application Data (63) Continuation-in-part of application No. PCT/US00/07095, filed on Mar. 15, 2000.
(60) Provisional application No. 60/145,438, filed on Jul. 23, 1999, and provisional application No. 60/125,463, filed on Mar. 22, 1999.

(51) Int. Cl.[7] .................................................. C12P 21/06
(52) U.S. Cl. ........................................... 435/68.1; 435/6
(58) Field of Search ....................................... 435/6, 68.1

(56) References Cited

U.S. PATENT DOCUMENTS

| 4,199,498 A | | 4/1980 | Zappelli et al. ........ 260/112.5 R |
| 4,282,352 A | | 8/1981 | Imahori et al. ................ 536/27 |
| 5,593,856 A | * | 1/1997 | Choi et al. ................. 435/68.1 |
| 5,801,006 A | | 9/1998 | Kaufman ..................... 435/15 |
| 6,168,931 B1 | * | 1/2001 | Swartz et al. .............. 435/68.1 |

FOREIGN PATENT DOCUMENTS

| WO | WO-00/55353 | * | 9/2000 | ........... C12P/21/06 |

OTHER PUBLICATIONS

Iglewski et al., Protein Engineering 6 (Suppl), 33 (1993).*
Endo et al. (1992), "Production of an Enzymatic Active protein Using a Continuous Flow Cell–Free Translation System." *Journal of Biotechnology*, vol. 25:221–230.
Kawarsaki et al. (1995), "A Long–Lived Batch Reaction System of Cell–Free Protein Synthesis." *Analytical Biochemistry*, vol. 226:320–324.
Kigawa et al. (1999), "Cell–free production and stable–isotope labeling of milligram quantities of proteins." *FEBS Letters*, vol. 442:15–19.
Kigawa et al. (1991), "Continuous Cell–Free Protein Synthesis System for Coupled Transcription–Translation." *J. Biochem.*, vol. 110:166–168.
Kim et al. (1996), "A highly efficient cell–free protein synthesis system from *Escherichia coli*." *Eur. J. Biochem.*, vol. 239:881–886.
Kim et al. (1996), "A Semicontinuous Prokaryotic Coupled Transcription/Translation System using a Dialysis membrane." *Biotechnol. Prog.*, vol. 12:645–649.
Kudlicki et al. (1992), "High Efficiency Cell–Free Synthesis of Proteins: Refinement of the Coupled Transcription/Translation System." *Analytical Biochemistry*, vol. 206:389–393.
Lennon et al. (1977), "Role of NAD[30] in the Stimulation of Protein Synthesis in Rabbit Reticulocyte Lysates." *Archives of Biochemistry and Biophysics*, vol. 184:42–48.
Lennon et al. (1976), "The Effect of NAD[+]And NAD[+] Analogs on Protein Synthesis in Rabbit Reticulocytes: Replacment of the Energy Regenerating System." *Biochemical and Biophysical Research Communications*, vol. 72(2).
Nakano et al. (1996), "Highly productive cell–free protein synthesis system using condensed wheat–germ extract." *Journal of Biotechnology*, vol. 46:275–282.
Noren et al. (1989), "A General Method for Site–Specific Incorporation of Unnatural Amino Acids into Proteins." *Science*, vol. 244:182–188.
Patnaik etal. (1998), "E. coli–Based In Vitro Transcription/ Translation: In Vivo–Specific Synthesis Rates and High Yields in a Batch System." *BioTechniques*, vol. 24:862–868.
Snyder et al. (1991), "Effects of Polymanine Analogs on the Extent and Fidelity of In Vitro Polypeptide Synthesis." *Biochemical and biophysical Research Communications*, vol. 176(3):1383–1392.
Spirin et al. (1988), "A Continuous Cell–Free Translation System Capable of Producing Polypeptides in High Yield." *Science*, vol. 24:1162–1164.

* cited by examiner

Primary Examiner—Kenneth R. Horlick
(74) Attorney, Agent, or Firm—Pamela J. Sherwood; Bozicevic, Field & Francis LLP (57) ABSTRACT

Compositions and methods are provided for the enhanced in vitro synthesis of biological molecules where ATP is required for synthesis. Of particular interest is the synthesis of polymers, e.g. nucleic acids, polypeptides, and complex carbohydrates. Glycolytic intermediates or glucose are used as an energy source, in combination with added NADH or NAD[+].

17 Claims, 6 Drawing Sheets

VITRO PROTEIN SYNTHESIS USING GLYCOLYTIC INTERMEDIATES AS AN ENERGY SOURCE

CROSS-REFERENCE TO RELATED APPLICATIONS

This application claims priority to U.S. Provisional Application 60/145,438, filed Jul. 23, 1999; and is a continuation-in-part of International Application PCT/US00/07095, Filed Mar. 15, 2000; which claims priority to U.S. Provisional Application No. 60/125,463, filed Mar. 22, 1999.

INTRODUCTION

The directed synthesis of proteins and other biological macromolecules is one of the great achievements of biochemistry. The development of recombinant DNA techniques has allowed the characterization and synthesis of highly purified coding sequences, which in turn can be used to produce highly purified proteins, even though in native cells the protein may be available only in trace amounts. Polypeptide chains can be synthesized by chemical or biological processes. The biological synthesis may be performed within the environment of a cell, or using cellular extracts and coding sequences to synthesize proteins in vitro.

For several decades, in vitro protein synthesis has served as an effective tool for lab-scale expression of cloned or synthesized genetic materials. In recent years, in vitro protein synthesis system has been considered as an alternative to conventional recombinant DNA technology, because of disadvantages associated with cellular expression. In vivo, proteins can be degraded or modified by several enzymes synthesized with the growth of the cell, and after synthesis may be modified by post-translational processing, such as glycosylation, deamination or oxidation. In addition, many products inhibit metabolic processes and their synthesis must compete with other cellular processes required to reproduce the cell and to protect its genetic information.

Because it is essentially free from cellular regulation of gene expression, in vitro protein synthesis has advantages in the production of cytotoxic, unstable, or insoluble proteins. The over-production of protein beyond a predetermined concentration can be difficult to obtain in vivo, because the expression levels are regulated by the concentration of product. The concentration of protein accumulated in the cell generally affects the viability of the cell, so that over-production of the desired protein is difficult to obtain. In an isolation and purification process, many kinds of protein are insoluble or unstable, and are either degraded by intracellular proteases or aggregate in inclusion bodies, so that the loss rate is high.

In vitro synthesis circumvents many of these problems. Also, through simultaneous and rapid expression of various proteins in a multiplexed configuration, this technology can provide a valuable tool for development of combinatorial arrays for research, and for screening of proteins. In addition, various kinds of unnatural amino acids can be efficiently incorporated into proteins for specific purposes (Noren et al. (1989) Science 244:182–188). However, despite all its promising aspects, the in vitro system has not been widely accepted as a practical alternative, mainly due to the short reaction period, which causes a poor yield of protein synthesis, and to the high cost of the reaction components.

The development of a continuous flow in vitro protein synthesis system by Spirin et al. (1988) Science 242:1162–1164 proved that the reaction could be extended up to several hours. Since then, numerous groups have reproduced and improved this system (Kigawa et al. (1991) J. Biochem. 110:166–168; Endo et al. (1992) J. Biotechnol. 25:221–230. Recently, Kim and Choi (1996) Biotechnol. Prog. 12: 645–649, reported that the merits of batch and continuous flow systems could be combined by adopting a 'semicontinuous operation' using a simple dialysis membrane reactor. They were able to reproduce the extended reaction period of the continuous flow system while maintaining the initial rate of a conventional batch system. However, both the continuous and semi-continuous approaches require quantities of expensive reagents, which must be increased by a significantly greater factor than the increase in product yield.

Several improvements have been made in the conventional batch system (Kim et al. (1996) Eur. J. Biochem. 239: 881–886; Kuldlicki et al. (1992) Anal. Biochem. 206:389–393; Kawarasaki et al. (1995) Anal. Biochem. 226: 320–324). Although the semicontinuous system maintains the initial rate of protein synthesis over extended periods, the conventional batch system still offers several advantages, e.g. convenience of operation, easy scale-up, lower reagent costs and excellent reproducibility. Also, the batch system can be readily conducted in multiplexed formats to express various genetic materials simultaneously.

Recently, Patnaik and Swartz (1998) Biotechniques 24:862–868 reported that the initial specific rate of protein synthesis could be enhanced to a level similar to that of in vivo expression through extensive optimization of reaction conditions. It is notable that they achieved such a high rate of protein synthesis using the conventional cell extract prepared without any condensation steps (Nakano et al. (1996) J. Biotechnol. 46:275–282; Kim et al. (1996) Eur. J. Biochem. 239:881–886). Kigawa et al. (1999) FEBS Lett 442:15–19 report high levels of protein synthesis using condensed extracts and creatine phosphate as an energy source. Their result implies that further improvement of the batch system, especially in terms of the longevity of the protein synthesis reaction, would substantially increase the productivity for batch in vitro protein synthesis. However, the reason for the early halt of protein synthesis in the conventional batch system has remained unclear.

As shown from the above, both protein productivity and production amount are still low, which is an obstacle in implementing the industrialization of cell-free protein synthesis. Therefore, improvements are greatly required in terms of the total productivity of the protein by increasing the specific production rate and the length of system operation. Optimizing these conditions of great interest for development of commercial processes.

SUMMARY OF THE INVENTION

Compositions and methods are provided for the enhanced in vitro synthesis of protein molecules. Glycolytic intermediates or glucose are used as an energy source, in combination with NADH or $NAD^+$ added in catalytic quantities. Coenzyme A may also be included in the reaction mix. In addition, inhibition of enzymes catalyzing undesirable reactions is achieved by: addition of inhibitory compounds to the reaction mix; modification of the reaction mixture to decrease or eliminate the responsible enzyme activities; or a combination of the two.

DETAILED DESCRIPTION OF THE EMBODIMENTS

Compositions and methods are provided for the enhanced in vitro synthesis of protein molecules, by the use of glycolytic pathways in the generation of ATP to drive the reaction. In order to maintain activity of the glycolytic pathway in the reaction mix, $NAD^+$/NADH is added to the reaction. Exemplary is the use of glucose in combination with the enzyme hexokinase; pyruvate; or phosphoenol pyruvate (PEP) as the energy source. In a preferred embodiment, acetyl CoA is also included in the reaction mixture. The phosphate that is hydrolyzed from ATP is recycled during the glucose or pyruvate oxidation, thereby preventing a net accumulation of free phosphate, which can have an inhibitory effect on synthetic reactions.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Glucose or glycolytic intermediate energy source, as used herein, refers to compounds that provide energy for the synthesis of ATP from ADP, and which are part of the glycolytic pathway. These energy sources include glucose, glucose-1-phosphate, glucose-6-phosphate, fructose-6-phosphate, fructose-1,6-diphosphate, triose phosphate, 3-phosphoglycerate, 2-phosphoglycerate, phosphoenol pyruvate (PEP) and pyruvate. Preferred energy sources are PEP, pyruvate, and glucose-6-phosphate.

The energy sources may also be homeostatic with respect to phosphate, that is they do not result in the accumulation of inorganic phosphate. Such secondary sources of energy recycle the free phosphate generated by ATP hydrolysis. Instead of exogenous addition of a source of high energy phosphate bonds, the required high energy phosphate bonds are generated in situ, e.g. through coupling with an oxidation reaction. A homeostatic energy source will typically lack high energy phosphate bonds itself, and will therefore utilize free phosphate present in the reaction mix during ATP regeneration. Since inorganic phosphate can be an inhibitory by-product of synthesis, the period of time when synthesis is maintained in vitro can be extended. A homeostatic energy source may be provided in combination with an enzyme that catalyzes the creation of high energy phosphate bonds.

Exemplary glycolytic intermediates that are homeostatic for phosphate metabolism are pyruvate and glucose. When glucose is used, it is desirable to include the enzyme hexokinase if not already present in the cell extract. However, it has been found that in the presence of NADH, it is not necessary to include a regenerative enzyme, such as pyruvate oxidase.

The energy source may be supplied as a suitable biologically acceptable salt or as the free acid, e.g. pyruvic acid, where applicable. The final concentration of energy source at initiation of synthesis will usually be at least about 1 mM, more usually at least about 10 mM, and not more than about 1000 mM, usually not more than about 100 mM. Additional amounts may be added to the reaction mix during the course of synthesis to provide for longer reaction times.

Cofactors: exogenous cofactor NADH or $NAD^+$ (β-nicotinamide adenine dinucleotide) is added to the reaction mixture at a concentration of at least about 0.1 mM, preferably 0.2 to 1 mM, and usually not more than about 10 mM.

Optionally, acetyl CoA (acetyl coenzyme A) or coenzyme A is also included in the reaction mixture. Although not required for the use of glucose or glycolytic intermediates as an energy source, it has been found to enhance the reaction. The useful concentrations are at least about 0.05 mM, usually at least about 0.1 mM, and not more than about 1 mM, usually not more than about 0.5 mM.

Use of Glucose: Where the homeostatic energy source is glucose, an enzyme will be included in the reaction mixture to catalyze the formation of glucose-6-phosphate from glucose. Hexokinase, EC 2.7.1.1, is generally used for this purpose. Hexokinase is widely available commercially, and has been isolated and cloned from a number of species. Examples include the enzymes corresponding to SwissProt P27595, HXK1_BOVIN; P19367, HXK1_HUMAN; P17710, HXK1_MOUSE; P05708, HXK1_RAT; Q09756, HXK1_SCHPO; P04806, HXKA_YEAST; Q42525, HXK_ARATH; P50506, HXK_DEBOC; P80581, HXK_EMENI; P33284, HXK_KLULA; Q02155, HXK_PLAFA; Q26609, HXK_SCHMA.

Where glucose is the energy source, the reaction mix will comprise a concentration of hexokinase sufficient to maintain the ATP pool, usually at least about 0.1 U/ml, more usually at least about 1 U/ml, and preferably at least about 10 U/ml, where the unit definition is that 1 unit reduces 1 μmole of NAD per minute in a coupled assay system with glucose-6-phosphate dehydrogenase at 30° C., pH 8.0. It will be understood by one of skill in the art that higher concentrations may be present, although generally at less than about 1000 U/ml.

The hexokinase may be provided in the reaction mix in a variety of ways. Purified or semi-purified enzyme may be added to the reaction mix. Commercial preparations are available, or the enzyme may be purified from natural or recombinant sources according to conventional methods. The genetic sequences of hexokinases may be used as a source of recombinant forms of the enzyme, for example *S. cerevisiae*. hexokinase PII gene, accession number M14410; or hexokinase PII, accession number M14411, both described in Kopetzki et al. (1985) Gene 39:95–102, etc.

The enzyme may also be included in the extracts used for synthesis. For example, extracts can be derived from E. coli for protein synthesis. The E. coli used for production of the extracts may be genetically modified to encode a suitable hexokinase. Alternatively, where the synthetic reactions are protein synthesis, a template, e.g. mRNA encoding hexokinase, plasmid comprising a suitable expression construct of hexokinase, etc. may be spiked into the reaction mix, such that a suitable amount of hexokinase is produced during synthesis.

Use of Pyruvate and PEP: Aspartic acid and asparagine are formed from phosphoenol pyruvate. The enzyme phosphoenol pyruvate synthetase (pps) converts pyruvate into PEP and consumes 2 equivalents of high-energy phosphate bonds (as ATP is converted to AMP) per molecule of PEP synthesized. When pyruvate is being used as an energy source, this enzyme therefore has the potential to waste both pyruvate and ATP, thereby robbing the protein synthesis reaction of its energy supply.

Addition of oxalic acid, which has been reported to inhibit pps (Narindrasorasak and Bridger (1978) Can. J. Biochem. 56: 816–9), was able to extend the reaction period both in the PEP and pyruvate systems. With both pyruvate and PEP as energy sources, inhibiting pps with oxalic acid decreased the rate of asp/asn production and increased the protein yield. Oxalic acid is added at a concentration of at least about 0.5 mM, and not more than about 100 mM, usually at least about 1 mM, and preferably at a concentration of about 3 mM.

For efficient use of energy source in both the PEP and the pyruvate system, the genes for E. coli pyruvate oxidase, which converts pyruvate into acetate consuming oxygen, and/or phosphoenol pyruvate synthetase (pps) can be disrupted or otherwise inactivated. The coding sequence for E. coli phosphoenol pyruvate synthetase may be accessed in Genbank, no. X59381; and is also published in Niersbach et al. (1992) Mol. Gen. Genet. 231:332–336. The coding sequence for E. coli pyruvate oxidase may be accessed in Genbank, no. X04105; and is also published in Grabau and Cronan (1986) Nucleic Acids Res. 14:5449–5460.

In vitro synthesis: as used herein refers to the cell-free synthesis of polypeptides in a reaction mix comprising biological extracts and/or defined reagents. The reaction mix will comprise at least ATP, an energy source; a template for production of the macromolecule, e.g. DNA, mRNA, etc.; amino acids, nucleotides and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

Reaction mix: as used herein refers to a reaction mixture capable of catalyzing the synthesis of polypeptides from a nucleic acid template. The mixture may comprise metabolic inhibitors that decrease undesirable enzymatic reactions. Alternatively, or in combination, the enhanced reaction mix will be engineered through genetic or other processes to decrease the enzymatic activity responsible for undesirable side-reactions, that result in amino acid depletion or accumulation.

In a preferred embodiment of the invention, the reaction mixture comprises extracts from bacterial cells, e.g. E. coli S30 extracts, as is known in the art. For convenience, the organism used as a source of extracts may be referred to as the source organism. While such extracts are a useful source of ribosomes and other factors necessary for protein synthesis, they can also contain small amounts of endogenous enzymes responsible for undesirable side-reactions that are unrelated to protein synthesis, but which deplete ATP, pyruvate or other reagents.

As used herein, the term endogenous is used to refer to enzymes, factors, etc. present in the extracts. Exogenous components are those that are introduced into the extracts through addition, and may be added at the time of synthesis, or may be added through genetic or other manipulation of the cells used as the starting material for extracts. For example, plasmids encoding an exogenous enzyme of interest may be added to the bacterial cells prior to preparation of the extracts.

Methods for producing active extracts are known in the art, for example they may be found in Pratt (1984), coupled transcription-translation in prokaryotic cell-free systems, p. 179–209, in Hames, B. D. and Higgins, S. J. (ed.), Transcription and Translation: a practical approach, IRL Press, New York. Kudlicki et al. (1992) Anal Biochem 206(2): 389–93 modify the S30 E. coli cell-free extract by collecting the ribosome fraction from the S30 by ultracentrifugation.

The extracts may be optimized for expression of genes under control of a specific promoter, (for example see Nevin and Pratt (1991) FEBS Lett 291(2):259–63, which system consists of an E. coli crude extract (prepared from cells containing endogenous T7 RNA polymerase) and rifampicin (an E. coli RNA polymerase inhibitor)). Kim et al. (1996) Eur. J. Biochem. 239: 881–886 further enhance protein production by optimizing reagent concentrations.

The reaction mix may comprise metabolic inhibitors of the undesirable enzyme activity. Frequently such inhibitors will be end-products of the reaction, that then inhibit by a feedback mechanism. The specific inhibitors are determined based on the metabolic pathways of the source organism. These pathways are well-known in the art for many bacterial and eukaryotic species, e.g. E. coli, S. cerevisiae, H. sapiens, etc. The inhibitor is added at a concentration sufficient to inhibit the undesirable enzymatic activity while increasing protein synthesis. Pathways of particular interest relate to the metabolism of pyruvate in E. coli cells, including the synthesis of aspartate from oxalacetate.

In an alternative embodiment to adding metabolic inhibitors, the undesirable enzymes may be removed or otherwise deleted from the reaction mix. In one embodiment of the invention, the coding sequence for the enzyme is "knocked-out" or otherwise inactivated in the chromosome of the source organism, by deletion of all or a part of the coding sequence; frame-shift insertion; dominant negative mutations, etc. The genomes of a number of organisms, including E. coli, have been completely sequenced, thereby facilitating the genetic modifications. For example, a markerless knockout strategy method is described by Arigoni et al. (1998) Nat Biotechnol 16(9)851–6.

A preferred method for inactivating targeted genes is described by Hoang et al. (1998) Gene 212:77–86. In this method, gene replacement vectors are employed that contain a tetracycline resistance gene and a gene encoding levan sucrase (sacB) as selection markers for recombination. The target gene is first cloned and mutagenized, preferably by deleting a significant portion of the gene. This gene is then inserted by ligation into a vector designed for facilitating chromosomal gene replacement. The E. coli cells are then transformed with those vectors. Cells that have incorporated the plasmid into the chromosome at the site of the target gene are selected, then the plasmid is forced to leave the chromosome by growing the cells on sucrose. Sucrose is toxic when the sacB gene resides in the chromosome. The properly mutated strain is selected based on its phenotype of tetracycline sensitivity and sucrose resistance. PCR analysis or DNA sequencing then confirms the desired genetic change.

However, in some cases the enzyme reducing the duration and yield of the protein synthesis reaction may be essential for the growth of the source organism. In those cases, a conditional knock-out may be used. For example, anti-sense sequences corresponding to the targeted gene are introduced into the source organism on an inducible promoter. The cells are grown for a period of time, and then the anti-sense construct induced, in order to deplete the cell of the targeted enzyme.

The enzyme can be removed from the cell extract after cell disruption and before use. Any of the several means known in the art of protein purification may be used, including affinity purification techniques such as the use of antibodies or antibody fragments with specific affinity for the target enzymes; use of affinity tags expressed as part of the target enzymes to facilitate their removal from the cell extract; and conventional purification methods.

In another embodiment, an antibody or antibody fragment (e.g., Fab or scFv) is selected for specific affinity for the target enzyme using phage display or other well developed techniques. That antibody or antibody fragment is then immobilized on any of several purification beads or resins or membranes using any of several immobilization techniques. The immobilized antibody is contacted with the cell extract to bind to the target enzyme, and the immobilized antibody/enzyme complex then removed by filtration or gentle centrifugation.

For example, the coding sequence of the targeted protein may be modified to include a tag, such as the Flag® extension (developed by Immunex Corp. and sold by Stratagene), or a poly-histidine tail. Many other examples have been published and are known to those skilled in the art. The tagged proteins are then removed by passage over the appropriate affinity matrix or column. The amino acid extension and binding partner are chosen so that only specific binding occurs under conditions compatible with the stability of the cell extract, and without significantly altering the chemical composition of the cell extract.

In yet another example, the target enzyme or enzymes are separated by any of several methods commonly used for protein purification, such as substrate affinity chromatography, ion exchange chromatography, hydrophobic interaction chromatography, electrophoretic separation, or other methods practiced in the art of protein purification.

Methods for In Vitro Synthesis

The subject system is useful for in vitro protein synthesis, which may include the transcription of RNA from DNA or RNA templates. The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include wheat germ extracts (Roberts et al. (1973) P.N.A.S. 70:2330), reticulocyte extracts (Pelham et al. (1976) Eur. J. Biochem. 67:247), E. coli extracts, etc., which can be treated with a suitable nuclease to eliminate active endogenous mRNA.

In addition to the above components such as cell-free extract, genetic template, amino acids and energy sources, materials specifically required for protein synthesis may be added to the reaction. These materials include salt, polymeric compounds, cyclic AMP, inhibitors for protein or nucleic acid degrading enzymes, inhibitor or regulator of protein synthesis, oxidation/reduction adjuster, non-denaturing surfactant, buffer component, spermine, spermidine, etc.

The salts preferably include potassium, magnesium, ammonium and manganese salt of acetic acid or sulfuric acid, and some of these may have amino acids as a counter anion. The polymeric compounds may be polyethylene glycol, dextran, diethyl aminoethyl, quaternary aminoethyl and aminoethyl. The oxidation/reduction adjuster may be dithiothreitol, ascorbic acid, glutathione and/or their oxides. Also, a non-denaturing surfactant such as Triton X-100 may be used at a concentration of 0–0.5 M. Spermine and spermidine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5–10 and a temperature of 20°–50° C., and more preferably, in the range of pH 6–9 and a temperature of 25°–40° C.

When using a protein isolating means in a continuous operation mode, the product output from the reactor flows through a membrane into the protein isolating means. In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use. Alternately, the protein product may be absorbed using expanded bed chromatography, in which case a membrane may or may not be used.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine or $^3$H-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

EXAMPLE 1

Figure 1:
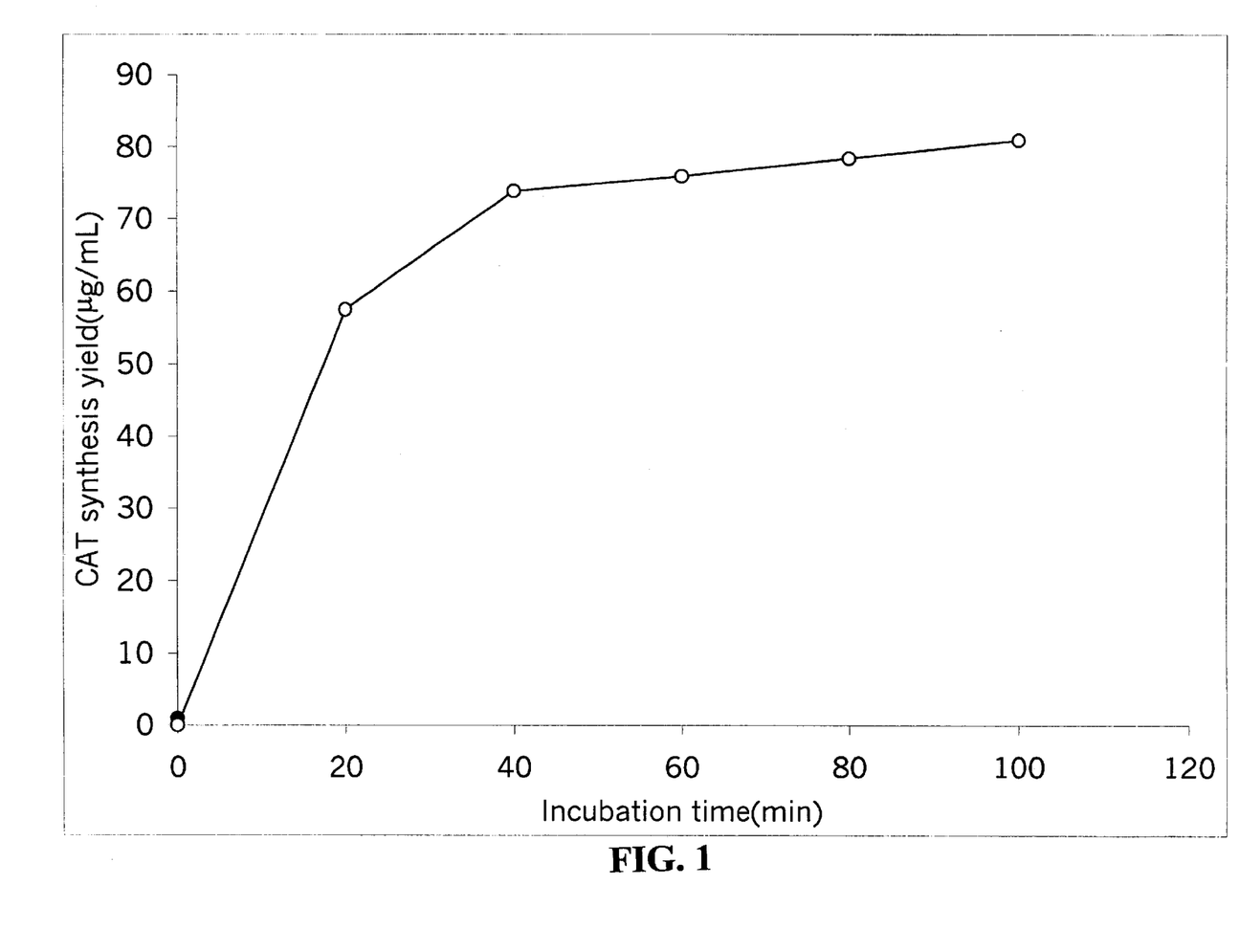
FIG. 1 is a graph illustrating the synthesis of chloramphenicol acetyl transferase using pyruvate as a secondary energy source.

Pyruvate, glucose or glycolytic intermediates can provide the energy for ATP regeneration, even in the absence of any exogenous enzymes. When pyruvate was added to a cell-free protein synthesis system along with an appropriate concentration of NADH, it supported protein synthesis for a significant yield (FIG. 1). Interestingly, pyruvate was effective only when it was added with NADH, and the addition of pyruvate alone was not sufficient to drive the synthesis reaction. The addition of acetyl-CoA further increased the yield to the level for a conventional system using phosphoenol pyruvate (PEP).

While not limiting to the subject matter of the invention, two pathways may be proposed for the mechanism of action, whereby pyruvate provides ATP regeneration potential to the synthesis reaction. In the first pathway, ATP regeneration is accomplished through an electron transport phosphorylation reaction. Since the extract is prepared from a total cell lysate, it is likely that the extract contains inverted membrane vesicles with the respiratory chain components properly embedded. Thus, after its conversion into acetyl-CoA by the endogenous pyruvate dehydrogenase complex, the pyruvate enters the TCA cycle to regenerate NADH, which in turn regenerates ATP using the respiratory chain and the F1F0 ATPase.

In a second proposed pathway, the generated acetyl-CoA is converted to acetyl phosphate by phosphotransacetylase. The resulting acetyl phosphate is then used for ATP regeneration. In either case, the oxidation of pyruvate provides the energy for ATP generation without accumulating any harmful by-products, and exogenous enzyme is not required. Alternatively, phosphoenol pyruvate can be used as the energy source, combining both the energy obtained by glycolysis and energy obtained from in situ ATP generation.

Figure 2:
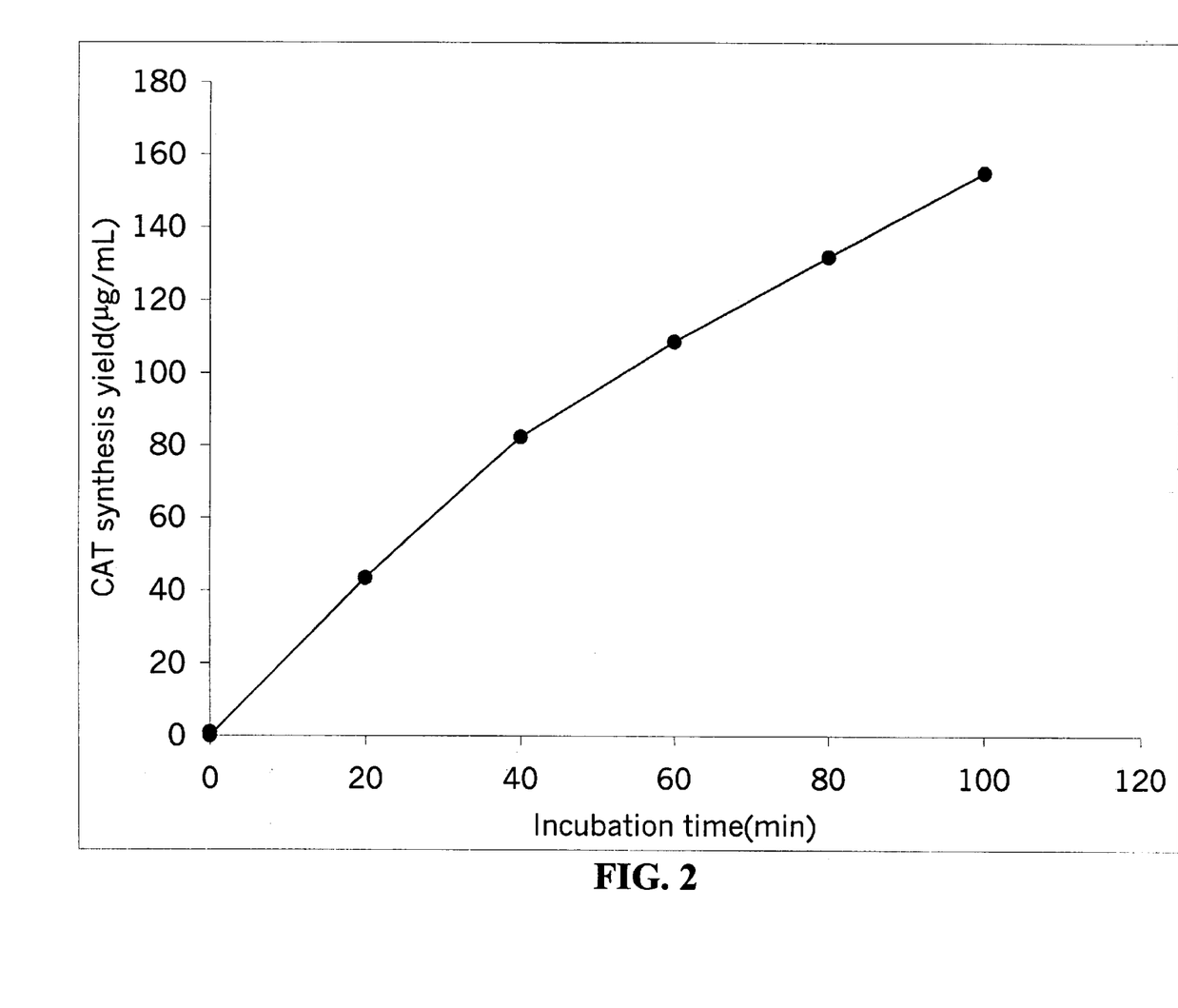
FIG. 2 is a graph illustrating the synthesis of chloramphenicol acetyl transferase using glucose-6-phosphate as a secondary energy source.

Since pyruvate is the terminal product of glycolysis, it was further investigated if other glycolytic intermediates can be used as an energy source for synthesis reactions. Strikingly, when glucose-6-phosphate, the first intermediate of glycolysis, was added to the cell-free synthesis system, in the presence of NADH, it does support protein synthesis (FIG. 2). Thus, it appears that all the enzymes required for the glycolytic pathway are active under the present conditions for protein synthesis. One can therefore use glucose, an even cheaper energy source, in combination with the enzyme hexokinase, to provide the ATP required for protein synthesis.

Materials and Methods

The standard reaction mixture for cell-free protein synthesis employing the conventional ATP regeneration system consists of the following components: 57 mM Hepes-KOH (pH 8.2), 1.2 mM ATP, 0.85 mM each of GTP, UTP and CTP, 1 mM DTT, 0.64 mM cAMP, 200 mM potassium glutamate, 80 mM $NH_4(OAc)$, 15 mM $Mg(OAc)_2$, 34 µg/ml folinic acid, 6.7 µg/ml plasmid, 33 µg/ml T7 RNA polymerase, 500 µM each of 20 unlabeled amino acids and [$^3$H] leucine (0.27GBq/mmol), 2% PEG 8000, 30 mM PEP (phosphoenolpyruvate), and 0.24 volumes of S30 extract.

T7 RNA polymerase was prepared from the culture of *E. coli* strain BL21(pAR1219) according to the slightly modified procedures of Davanloo et al. (1984) Proc. Natl. Acad. Sci. U.S.A. 81: 2035–2039).

S30 extract was prepared from wild type or genetically modified *E. coli* K12 (strain A19) according to the procedures reported earlier (Pratt, In Hames, B. D. and Higgins, S. J. (ed.), Transcription and translation: a practical approach. IRL Press, New York (1984) pp 179–209).

In the reaction using pyruvate and pyruvate oxidase to regenerate ATP, PEP was replaced with the following components: 33 mM pyruvate, 6 U/ml pyruvate oxidase, 6.7 mM potassium phosphate, 3.3 mM TPP.

In the new system developed in this invention, instead of PEP, 33 mM sodium pyruvate or the same concentration of glucose-6-phosphate was added to the reaction mixture along with 0.3 mM NADH (β-nicotinamide adenine dinucleotide). In some cases, 0.2 mM acetyl-CoA was added to enhance the protein synthesis. Reactions were conducted for 2 hours in a water bath set at 37° C.

Analysis Methods for Synthesized Proteins

The amount of synthesized protein was estimated from the measured cold TCA-insoluble radioactivities as described (Kim et al. (1996) Eur. J. Biochem. 239: 881–886). Radioactivities of samples were measured in a liquid scintillation counter(LS3801, Beckman).

EXAMPLE 2

Depletion of Energy Source and Amino Acids

Methods

The standard reaction mixture for the PEP system produces a base level of protein expression (approx. 100 μg/ml or 13.8 μg/mg cellular protein) and consists of the following components:

57 mM Hepes-KOH (pH 8.2), 1.2 mM ATP, 0.85 mM each of GTP, UTP and CTP, 1 mM DTT, 0.64 mM cAMP, 200 mM potassium glutamate, 80 mM $NH_4(OAc)$, 15 mM $Mg(OAc)_2$, 34 Mg/ml folinic acid, 6.7 μg/ml plasmid, 33 μg/ml T7 RNA polymerase, 500 μM each of 20 unlabeled amino acids, [$^3$H] leucine (0.27GBq/mmol), 2% PEG 8000, 30 mM PEP (phosphoenol pyruvate), and 0.24 volumes of S30 extract.

T7 RNA polymerase was prepared from the culture of *E. coli* strain BL21 (pAR1219) according to the slightly modified procedures of Davanloo et al. (1984) Proc. Natl. Acad. Sci. U.S.A. 81: 2035–2039. S30 extract was prepared from wild type *E. coli* K12 (strain A19) according to the procedures reported earlier (Kim et al., supra.). The standard reaction mixture for the pyruvate system is nearly identical. The PEP is omitted and in its place is added: 33 mM pyruvate, 6 U/ml pyruvate oxidase, 6.7 mM potassium phosphate, and 3.3 mM TPP (thiamine pyrophosphate).

Reactions were conducted for given time periods in a water bath set at 37° C. The amount of synthesized protein was estimated from the measured cold TCA-insoluble radioactivities as described (Kim et al, supra.) Radioactivities of samples were measured in a liquid scintillation counter (Beckman). SDS-PAGE analysis was carried out using a 16% SDS-PAGE gel (NOVEX) with standard molecular weight markers. Expressed proteins were visualized by standard Coomassie Blue staining method.

Early experiments had indicated that protein synthesis stopped with the PEP system after about 30 minutes, and after about 200 minutes for the pyruvate system. However, calculations suggested that insufficient protein had been synthesized to account for depletion of the required reagents. To investigate the cause of synthesis cessation, pre-incubation experiments were employed. In these experiments, no DNA template was added and the measurement of radioactive leucine incorporation showed that insignificant protein synthesis occurred. The pre-incubation was conducted for various time periods after which the DNA template was added and protein synthesis measured after a one-hour incubation period. Activity could only be restored by a second addition of the energy source, PEP, and the 20 amino acids (see FIG. 3).These surprising results showed that both the energy source and the amino acids are inactivated independent of protein synthesis.

EXAMPLE 3

Oxalic Acid Increases Protein Production

These data show that oxalic acid, most likely by inhibiting PEP synthase (pps), slows the rate of aspartic acid/asparagine accumulation and also increases the yield of protein.

Formation of certain amino acids can significantly diminish the energy available for protein synthesis. In the case of alanine, pyruvate is being directly converted in a reaction with glutamate that is catalyzed by alanine-glutamate transaminase. This reaction directly consumes the energy source in the pyruvate system.

With aspartic acid and asparagine formation, the consequences are even more serious. These amino acids are formed from oxaloacetate which, in turn, is derived from PEP. For a PEP system, this is a direct drain of the energy source. For the pyruvate system, the formation of these amino acids indicates that pyruvate is being converted to PEP. This will decrease the amount of pyruvate available for the pyruvate oxidase reaction. However, even more serious is the realization that this conversion requires the conversion of ATP to AMP. For every mole of PEP that is generated and used for amino acid synthesis, two moles of ATP and one mole of pyruvate are lost.

Figure 3:
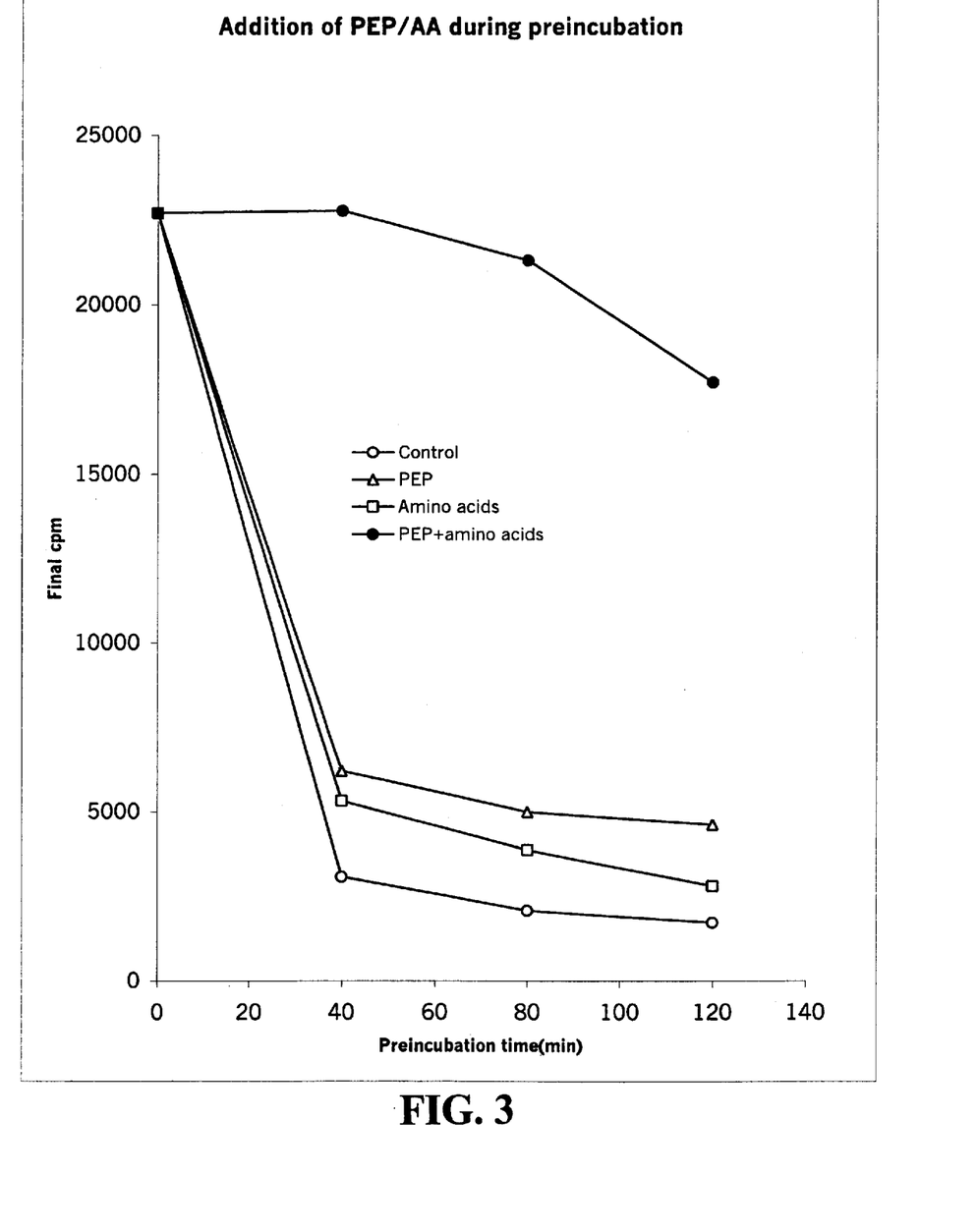
FIG. 3 is a graph showing the effects of adding amino acids and energy source after pre-incubation.
Figure 4:
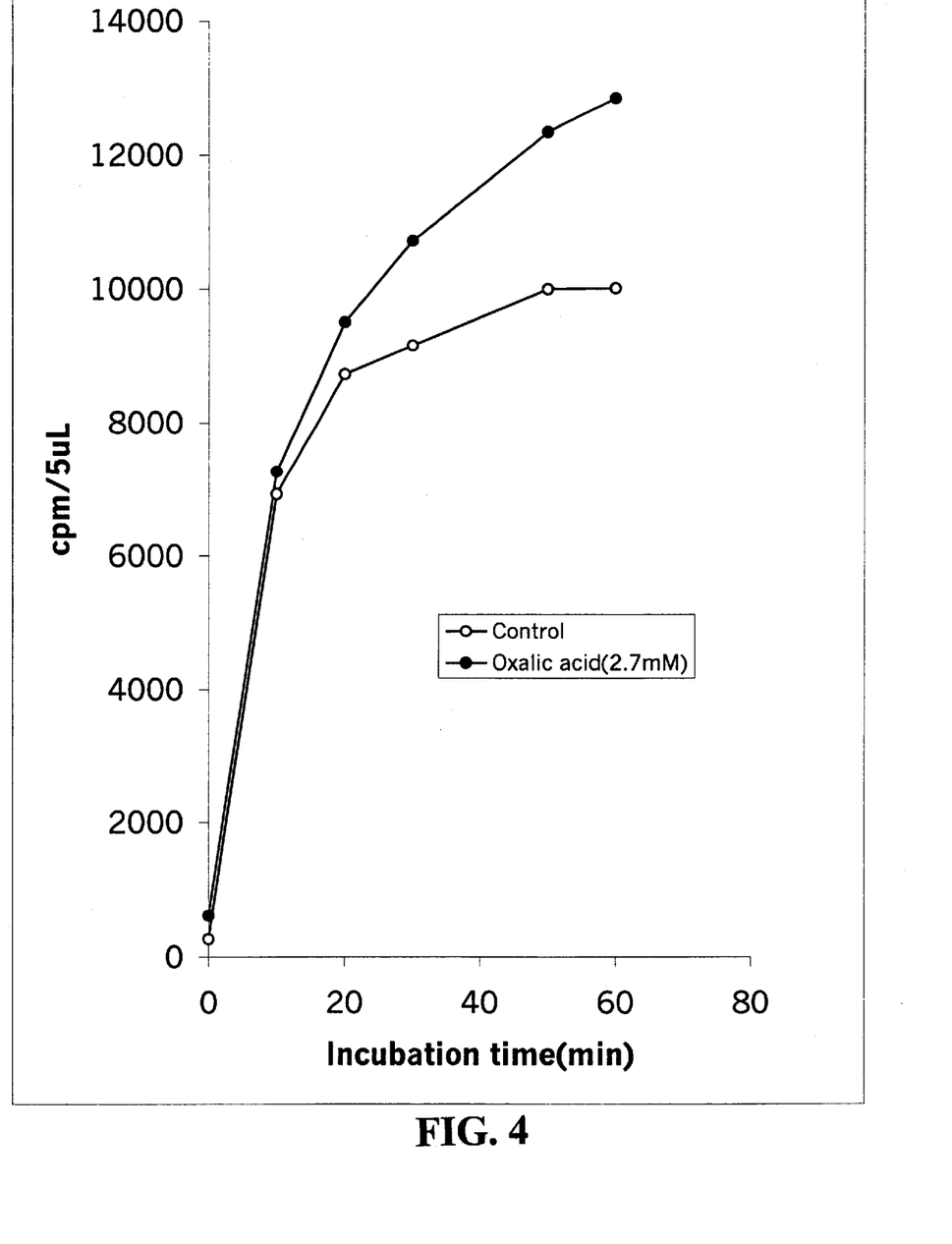
FIG. 4 is a time course of protein synthesis using phosphoenol pyruvate as an energy source, with or without oxalic acid.
Figure 5:
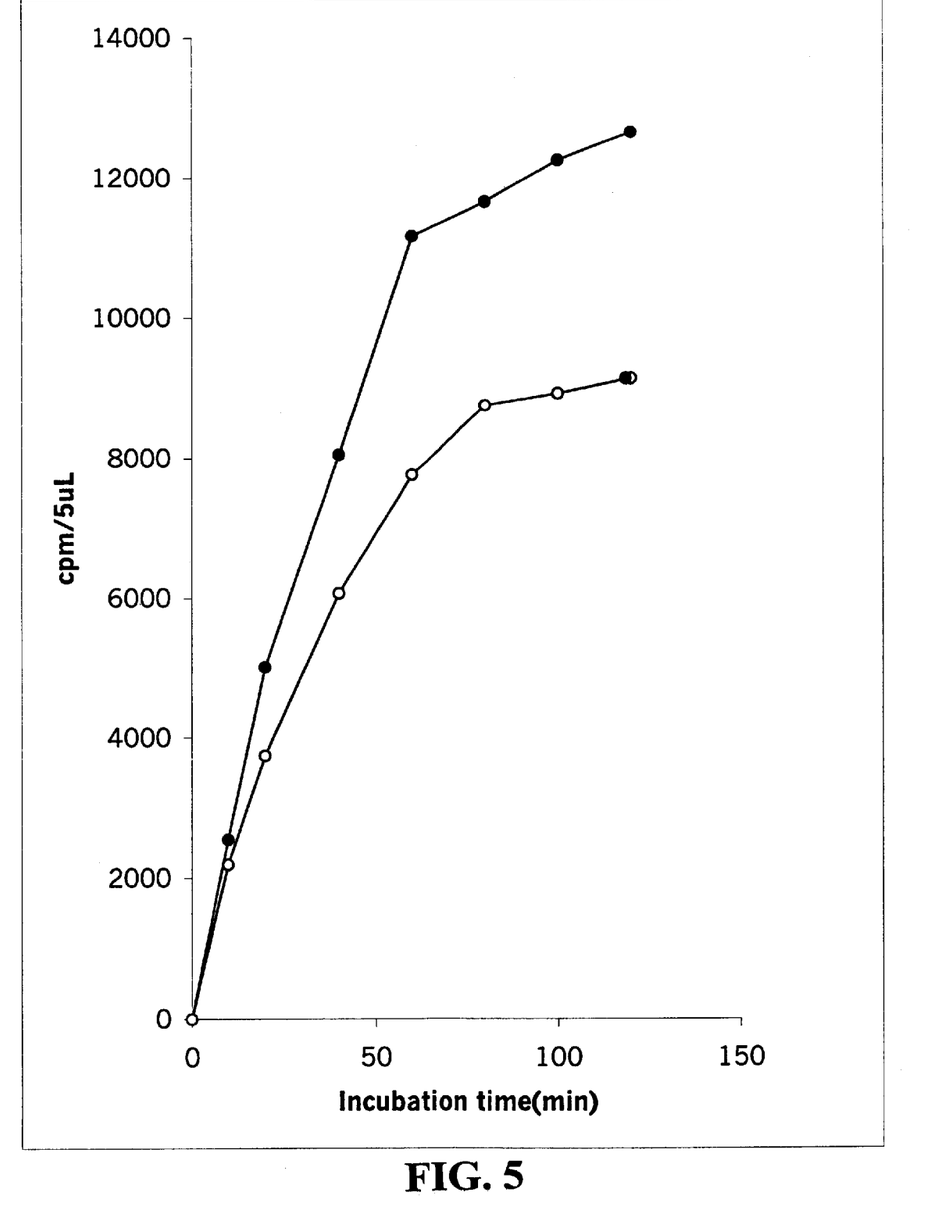
FIG. 5 is a time course of protein synthesis using pyruvate as an energy source, with or without oxalic acid.

The conversion of pyruvate to PEP is catalyzed by the enzyme, phosphoenol pyruvate synthetase (pps). Oxalic acid has been reported to inhibit pps. To test to see if the pps reaction is indeed responsible for aspartic acid and asparagine synthesis and to test if these reactions are reducing the protein yield, 2.7 mM oxalic acid was added to both the pyruvate system and the PEP system. FIGS. 3 and 4 show that oxalic acid increases the protein yield in both systems. With the pyruvate system, less pyruvate and ATP are being lost to amino acid formation. In the case with PEP as the energy source, pyruvate is the direct product after PEP transfers its phosphate to ADP. That pyruvate will then be converted back into PEP by pps, but at the cost of two ATP's for each new PEP molecule. Thus, even with PEP as the initial energy source, the enzyme, pps wastes ATP. With both pyruvate and PEP as energy sources, inhibiting pps with oxalic acid provided a significant benefit by increasing product yield.

EXAMPLE 4

Reaction Mix Optimization

Several features of the previous experiments were combined in an optimized reaction mix. 2.7 mM oxalate decreased aspartate/asparagine accumulation and also increased protein yield. The glycolytic enzyme approach was used in the PEP system, since pyruvate is the product of the pyruvate kinase reaction. Finally, to avoid amino acid depletion, the initial concentration of amino acids was increased to 2 mM.

This combination of 33 mM PEP, 0.33 mM $NAD^+$, 0.26 mM CoA, 2.7 mM oxalic acid, and 2 mM amino acids produced striking results for a 15 μl-batch reaction. With n=4, the average yield of CAT was 513 μg/ml as judged by $^{14}$C leucine incorporation. The CAT band was easily visible on a Coomasie blue stained PAGE gel. Also the measured enzymatic activity suggests an even higher yield based on the published CAT specific activity and the observation that approximately 30–40% of the synthesized CAT is insoluble.

EXAMPLE 5

Scale-up Protocol

Figure 6:
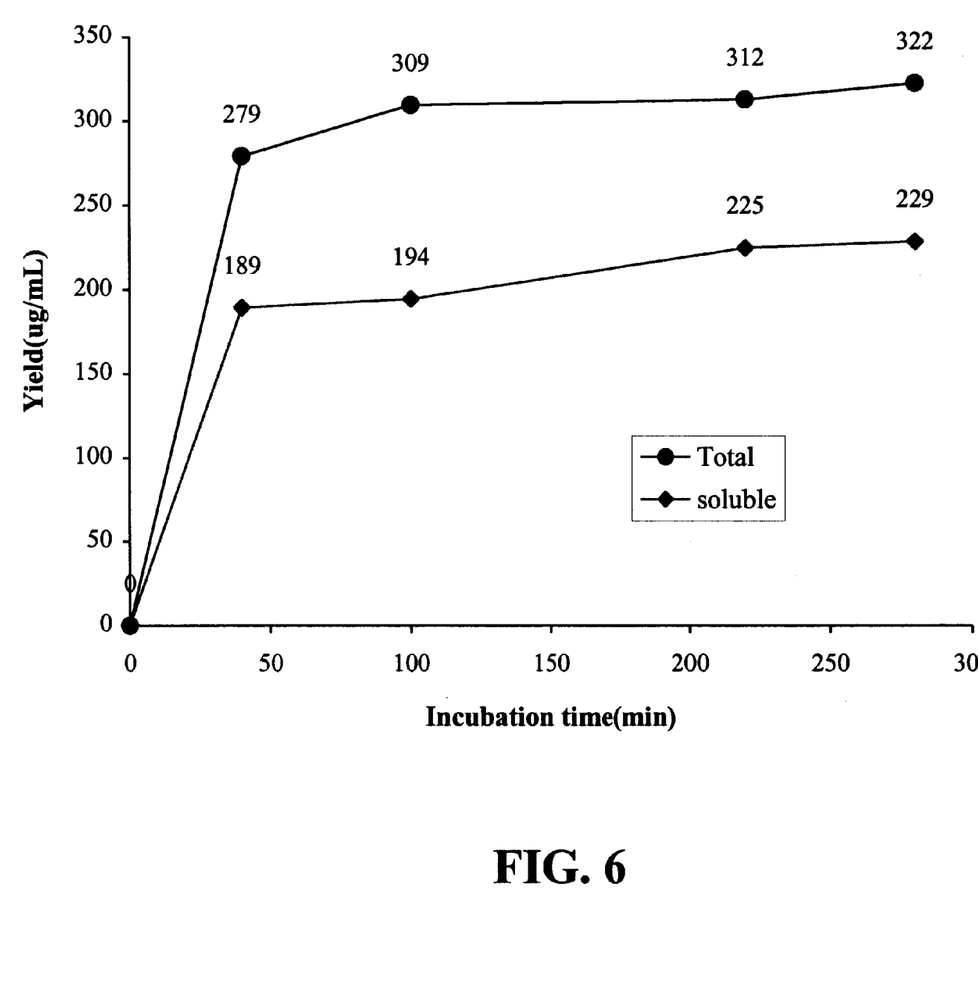
FIG. 6 is a time course of chloramphenicol acetyl transferase synthesis in 6-ml batch reaction.

The scale-up of the batch technique described in Example 4 was straightforward. The reaction was increased to a 6-ml volume in a glass vial with mixing provided by a standard magnetic stir bar. As described above, all of the ATP was generated from a single addition of 33 mM PEP. As before, 2 mM amino acids, 0.33 mM NAD$^+$, 0.26 mM CoA and 2.7 mM oxalate were added in addition to the normal components. The total yield was 77 nmoles of CAT as measured by $^{14}$C leucine incorporation. This time, 68±4% of the CAT was soluble (for four time points). Enzyme activity suggested a higher yield; 102 nmoles produced in the first 40 minutes. (This is calculated based on the observation that 32% of the CAT was insoluble and, therefore, presumably inactive; and on the published CAT specific activity of 125 units/mg) Only an additional 16 nmoles of CAT were made over the next four hours. The CAT yields (based on $^{14}$C leucine counts) for the time samples are shown in FIG. 6.

What is claimed is:

1. A method for in vitro synthesis of biological macromolecules, the method comprising:
   synthesizing a biological macromolecule in a synthesis reaction utilizing ATP as a primary energy source;
   adding to said synthesis reaction NADH or NAD$^+$ in combination with a glucose or a glycolytic intermediate, which provide energy for the synthesis of ATP from ADP.

2. The method of claim 1, wherein said glucose or a glycolytic intermediate is pyruvate.

3. The method of claim 1, wherein said glucose or a glycolytic intermediate is glucose, and said synthesis reaction further comprises the enzyme hexokinase.

4. The method of claim 1, wherein said glucose or a glycolytic intermediate is glucose 6-phosphate.

5. The method of claim 1, wherein said glucose or a glycolytic intermediate is phosphoenol pyruvate.

6. The method of claim 1, wherein said synthesis reaction further comprises acetyl CoA or coenzyme A.

7. The method of claim 1, wherein said glucose or a glycolytic intermediate is present at an initial concentration of at least about 1 mM.

8. The method of claim 1, wherein said glucose or a glycolytic intermediate is present at an initial concentration of at least about 10 mM.

9. The method of claim 3, wherein said hexokinase is present at an initial concentration of at least about 0.5 U/ml.

10. The method of claim 1, wherein said synthesis reaction comprises a metabolic inhibitor of pyruvate metabolism.

11. The method of claim 10, wherein said inhibitor comprises oxalic acid.

12. The method of claim 1, wherein said synthesis reaction comprises an *E. coli* extract deficient in the enzyme phosphoenol pyruvate synthetase.

13. The method of claim 1, wherein said synthesis of biological macromolecules comprises translation of mRNA to produce polypeptides.

14. The method of claim 13 wherein said synthesizing of biological macromolecules comprises transcription of mRNA from a DNA template.

15. The method of claim 1 wherein said synthesizing of biological macromolecules is performed as a batch reaction.

16. The method of claim 1, wherein said synthesizing of biological macromolecules is performed as a continuous reaction.

17. The method of claim 15 wherein said glucose or a glycolytic intermediate is added at intervals during said batch reaction.

* * * * *